United States Patent [19]

Oberlinner

[11] Patent Number: 4,611,070

[45] Date of Patent: Sep. 9, 1986

[54] SPIRODIBENZOPYRANS

[75] Inventor: Andreas Oberlinner, Ludwigshafen, Fed. Rep. of Germany

[73] Assignee: BASF Aktiengesellschaft, Rheinland, Fed. Rep. of Germany

[21] Appl. No.: 336,703

[22] Filed: Jan. 4, 1982

Related U.S. Application Data

[63] Continuation of Ser. No. 90,409, Nov. 1, 1979, abandoned.

[30] Foreign Application Priority Data

Nov. 3, 1978 [DE] Fed. Rep. of Germany ....... 2847690

[51] Int. Cl.[4] .......................................... C07D 311/58
[52] U.S. Cl. ...................... 549/344; 544/70; 546/15; 549/525
[58] Field of Search .......................... 544/70; 549/344

[56] References Cited

U.S. PATENT DOCUMENTS 3,899,514 8/1975 Baumann et al.
4,147,509 4/1979 Baumann et al. ............ 427/151
4,161,589 7/1979 Baumann et al. ............ 544/70

OTHER PUBLICATIONS

Kirk–Othmer, *Encyclopedia of Chemical Technology*, vol. 8, third ed., pp. 348–349.

*Primary Examiner*—Robert W. Ramsuer
*Attorney, Agent, or Firm*—Oblon, Fisher, Spivak, McClelland & Maier

[57] ABSTRACT

Dye-forming components of the general formula

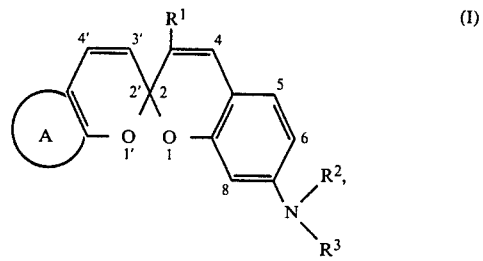

where A is the radical of a fused benzo ring or 2,1-naphthalene ring, and either radical may be substituted by $C_1$–$C_4$-alkyl, $C_1$–$C_4$-alkoxy, nitro, chlorine, bromine or $C_1$–$C_6$-alkoxycarbonyl, $R^1$ is $C_1$–$C_{16}$-alkyl, $C_7$–$C_{10}$-phenylalkyl or phenyl which is unsubstituted or substituted by $C_1$–$C_4$-alkyl, $C_1$–$C_4$-alkoxy, chlorine or bromine, and $R^2$ and $R^3$ independently of one another are hydrogen, $C_1$–$C_{12}$-alkyl, $C_2$–$C_4$-alkyl, which is substituted by cyano, chlorine, methoxy or ethoxy, $C_5$–$C_7$-cycloalkyl, $C_7$–$C_{10}$-phenylalkyl or trimethylene which is unsubstituted or substituted by 1, 2 or 3 methyl groups and is bonded to the carbon in the 6- and/or 8-position of the benzo ring, or $R^2$ is $C_1$–$C_4$-alkyl and $R^3$ is phenyl which is unsubstituted or substituted by chlorine, bromine, $C_1$–$C_3$-alkyl, methoxy or ethoxy, or $R^2$ is benzyl and $R^3$ is β-cyanoethyl, or

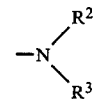

is morpholinyl, pyrrolidinyl, N'—$C_1$–$C_4$-alkylpiperazinyl or isoindolinyl.

In contact with paper coated with electron acceptors the compounds (I) give violet or blue to green colorations, while on uncoated paper virtually no color is developed.

The compounds (I) may be used as dye-forming components for pressure-sensitive recording or copying materials.

3 Claims, No Drawings

SPIRODIBENZOPYRANS

This is a continuation of application Ser. No. 090,409, filed Nov. 1, 1979 now abandoned.

The present invention relates to dye-forming components of the general formula I

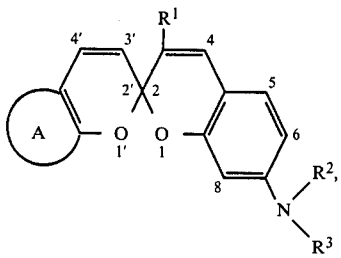

where

A is a radical of a fused benzo ring which is unsubstituted or substituted by $C_1$–$C_4$-alkyl, $C_1$–$C_4$-alkoxy, nitro, chlorine, bromine or $C_1$–$C_6$-alkoxycarbonyl, or is a radical of a 2,1-fused naphthalene ring, which is unsubstituted or substituted by chlorine, bromine or $C_1$–$C_6$-alkoxycarbonyl, $R^1$ is $C_1$–$C_{16}$-alkyl, phenyl which is unsubstituted or substituted by $C_1$–$C_4$-alkyl, $C_1$–$C_4$-alkoxy, chlorine or bromine, or $C_7$–$C_{10}$-phenylalkyl and $R^2$ and $R^3$ independently of one another are hydrogen, $C_1$–$C_{12}$-alkyl, $C_2$–$C_4$alkyl which is substituted by cyano, chlorine, methoxy or ethoxy, $C_5$–$C_7$-cycloalkyl, $C_7$–$C_{10}$-phenylalkyl or trimethylene which is unsubstituted or substituted by 1, 2 or 3 methyl groups and is bonded to the carbon in the 6- and/or 8-position of the benzo ring, or $R^2$ is $C_1$–$C_4$-alkyl and $R^3$ is phenyl which is unsubstituted or substituted by chlorine, bromine, $C_1$–$C_3$-alkyl, methoxy or ethoxy or $R^2$ is benzyl and $R^3$ is β-cyanoethyl, or the group

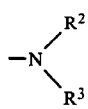

is morpholinyl, which is unsubstituted or substituted by 1 or 2 methyl groups, or is pyrrolidinyl, N'-$C_1$-$C_4$-alkyl-piperazinyl or isoindolinyl.

The spirodipyrans of the formula I are pale-colored or colorless compounds, the solutions of which, in an inert organic solvent, give colorations, in violet or blue to green hues, on contact with an electron-attracting substance. Typical examples of electron acceptors are carboxylic acids, mineral acids, kaolin, bentonite, activated clay, aluminum silicate, attapulgite or any other clay, acidic polymeric materials, eg. condensation products based on phenols and/or phenolsulfonic acids, and metal oxides or salts, eg. zinc oxide, aluminum oxide, zinc chloride, iron stearate and cobalt naphthenate.

Because of these properties, the novel compounds of the formula I can be used as dye-forming components for pressure-sensitive recording materials and copying materials.

The compounds according to the invention, of the formula I, have the advantage over the structurally isomeric compounds described in German Pat. No. 2,232,364 and possessing a substituent in the 3'-position that when used in pressure-sensitive copying systems the novel compounds exhibit virtually no tendency to produce a coloration on uncoated coating base paper. Hence, on making a copy, a mirror image does not appear on the back of the top sheet coated with the dye-forming component. For the same reason, in the event of unintentional destruction of the capsules, no staining of the side of the sheet which carries the microcapsule layer occurs.

Because of their absorption characteristics, the compounds according to the invention are very suitable for use conjointly with additional, yellow to red, dye-forming components in mixtures of dye-forming components which produce black copies.

For use in pressure-sensitive copying systems, it is advantageous to enclose the compounds according to the invention, in solution or suspension in an organic solvent, e.g. a chloroparaffin, halogenated or partially hydrogenated diphenyl, alkylbenzene, alkylnaphthalene, alkylated dibenzylbenzene, paraffin oil or mineral oil, or in a conventional solvent, eg. toluene or xylene, in microcapsules in the conventional manner, and then to coat the paper surface therewith. In contact with electron-attracting substance, an image in a violet or blue to green color is then produced on exposure to appropriate writing pressure or typing pressure.

Suitable processes for the manufacture of micro-capsules are described, for example, in U.S. Pat. Nos. 2,800,457 and 2,800,458 and in German Pat. No. 2,119,933.

Since the compounds (I) according to the invention are more stable, even in aqueous suspension, than the prior art dye-forming components, they give virtually colorless microcapsule dispersions.

It is also possible to produce a fine dispersion of the compounds according to the invention, of the general formula I, in wax or oil-wax mixtures, using the process described in U.S. Pat. No. 3,103,404, and to use such mixtures to coat base materials, eg. films or paper. Pressure-sensitive materials are obtained, which can be used for producing copies on papers coated with electron acceptors and which, after use, are removed like carbon paper.

For technical reasons, spirodipyrans of the formula

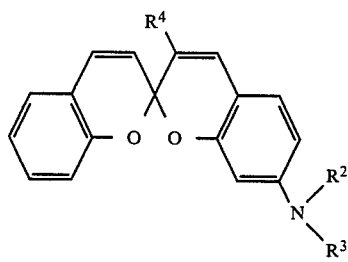

where $R^4$ is $C_1$–$C_4$-alkyl and $R^2$ and $R^3$ have the above meanings are preferred for use as dye-forming components.

From the point of view of their use in copying processes using pressure-sensitive materials, the following compounds are of particular importance:

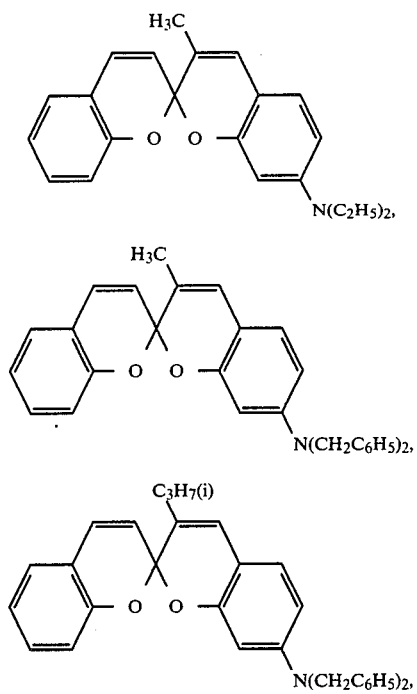

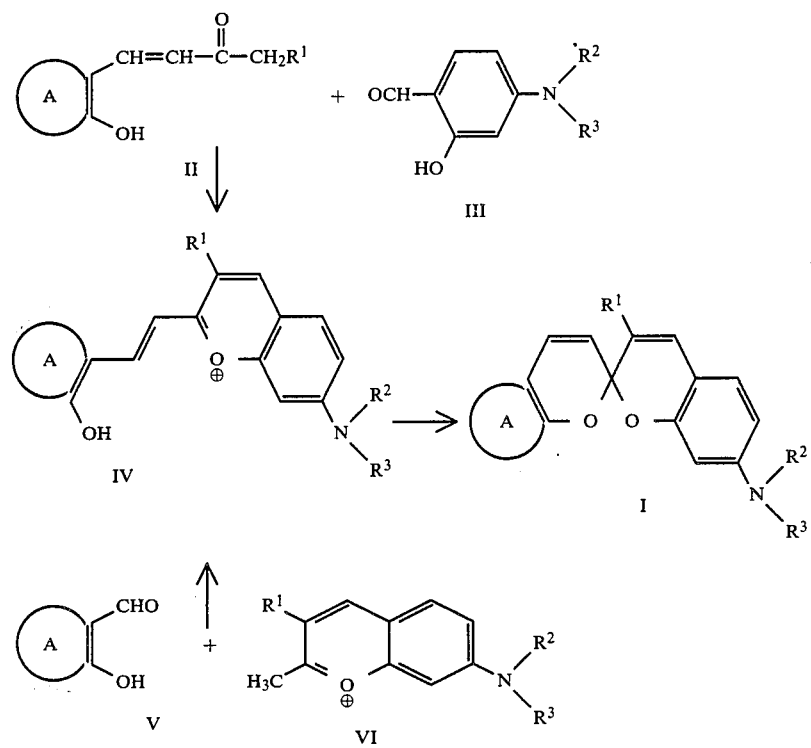

The dye-forming components are synthesized in the conventional manner, in accordance with the reaction scheme shown below, by cyclization of benzopyrylium compounds of the formula IV. The latter are obtained, for example, by condensing o-hydroxy-styryl compounds of the formula II with N-substituted p-aminosalicylaldehydes of the formula III. The compounds of the formula IV can also be prepared by reacting the benzopyrylium salts of the formula VI with aldehydes of the formula V in the conventional manner, in accordance with the scheme also shown below.

The condensation is advantageously carried out in an inert organic solvent, such as an alcohol, carboxylic acid, carboxylic acid anhydride, carboxylic acid amide or hydrocarbon, or in acetonitrile, in the presence or absence of an acidic or basic condensing agent, eg. zinc chloride, phosphoric acid, hydrogen chloride, toluenesulfonic acid, boric acid, pyridine, triethylamine or ammonium acetate, under conventional condensation conditions.

As a rule, the condensation is carried out at from 20° to 120° C.

The cyclization to give the pyran derivative may be carried out simultaneously with the condensation or subsequently thereto, in the same process step or in a separate process step, in the conventional manner, if appropriate in the presence of a base, such as sodium hydroxide or potassium hydroxide, sodium carbonate or potassium carbonate, sodium acetate or potassium acetate, ammonia, an aliphatic amine or pyridine. The crystalline spirodipyran compound which separates out from this solution can be used—either directly or after purification, eg. by recrystallization or reprecipitation—as a dye-forming component for copying processes.

Examples of suitable starting compounds, of the formulae II and III, or V and VI, for the preparation of the compound (IV), are:

(a) 2-hydroxy-styryl-ketones of the formula II: ethyl-(2-hydroxystyryl)-ketone, n-propyl-(2-hydroxystyryl)-ketone, isobutyl-(2-hydroxy-styryl)-ketone, ethyl(2-hydroxy-5-chloro-styryl)-ketone, ethyl-(2-hydroxy-5-bromo-styryl)-ketone, isopentyl-(2-hydroxy-styryl)-ketone, isooctyl-(2-hydroxy-styryl)-ketone and isohexyl-(2-hydroxy-styryl)-ketone.

(b) Aldehydes of the formula III: 4-N,N-dimethylaminosalicylaldehyde, 4-N,N-diethylaminosalicylaldehyde, 4-N,N-di-n-propylaminosalicylaldehyde, 4-N,N-didodecylaminosalicylaldehyde, 4-N,N-dibenzylaminosalicylaldehyde, 4-N,N-diphenethylaminosalicylaldehyde, 4-N-methyl-N-p-tolyl-aminosalicylaldehyde, 4-N-methyl-N-p-chlorophenyl-aminosalicylaldehyde, 4-N-pyrrolidylsalicylaldehyde, 4-N-piperidinyl-salicylaldehyde, 4-N-morpholinyl-salicylaldehyde, 4-N,N-di-β-chloroethylaminosalicylaldehyde, 4-N-β-methoxyethyl-N-methylaminosalicylaldehyde, 4-N-cyclohexyl-N-methylamino-salicylaldehyde, 4-N,N-di-β-cyanoethylamino-salicylaldehyde, 4-N-isoindolinyl-salicylaldehyde and 4-N-methyl-N-(p-methoxyphenyl)-amino-salicylaldehyde as well as the compounds of the formula

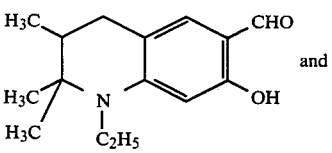

and

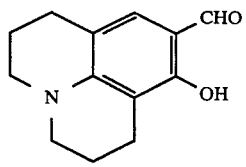

(c) Aldehydes of the formula V: salicylaldehyde, 2-hydroxy-1-naphthaldehyde, 6-chloro-2-hydroxy-1-naphthaldehyde, 6-bromo-2-hydroxy-1-naphthaldehyde, 8-methoxycarbonyl-2-hydroxy-1-naphthaldehyde, 8-ethoxycarbonyl-2-hydroxy-1-naphthaldehyde, 4-methoxysalicylaldehyde, 6-methoxycarbonylsalicylaldehyde, 5-tert.-butyl-salicylaldehyde and 5-nitro-salicylaldehyde.

(d) Benzopyrylium salts of the formula VI in the form of their chlorides, perchlorates, tetrafluoborates, tetrachloroferrates and trichlorozincates: A 2-methyl-3-phenyl-7-dimethylamino-benzopyrylium salt, 2-methyl-3-p-tolyl-7-dimethylamino-benzopyrylium salt, 2-methyl-3-p-chlorophenyl-7-dimethylamino-benzopyrylium salt, 2-methyl-3-p-methoxyphenyl-7-dimethylamino-benzopyrylium salt or 2-methyl-3-phenyl-7-N-pyrrolidinyl-benzopyrylium salt.

The Examples which follow illustrate the preparation and isolation of the novel spirodipyran compounds.

EXAMPLE 1

20 parts of isobutyl-(2-hydroxystyryl)-ketone, 14 parts of zinc chloride and 19 parts of 4-diethylaminosalicylaldehyde are dissolved in 80 parts of methanol. Hydrogen chloride is passed into the solution at 40°–50° C. until saturation is reached, and the mixture is then stirred for 12 hours at room temperature. The crystalline dye is isolated from the cooled reaction mixture and stirred in 150 parts of 25% strength ammonia solution and 250 parts of toluene until the mixture has turned completely pale. The toluene phase is separated off, dried with sodium sulfate and concentrated to one-third of its original volume. 100 parts of methanol are then added to this solution, thereby precipitating 20 parts of 3-isopropyl-7-diethylamino-2,2′-spirodi-(2H-1-benzopyran) of the formula

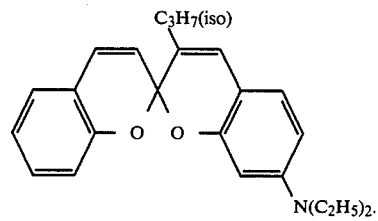

The compound melts at 140°–142° C.

A solution of this compound is micro-encapsulated and the capsules are coated onto paper. The paper is placed on an acid receptive coating and on writing on the paper the capsules are destroyed and their contents are brought into contact with the receptive coating, resulting in a bluish grey copy.

Because of the very limited capacity of the dye-forming component to develop a color without an acceptor, virtually no color (mirror image) is produced on the sheet carrying the capsule layer by the solution of dye-forming component released from the destroyed capsules.

The dye-forming component also exhibits this low tendency to produce a coloration when a copy is made on uncoated paper, where virtually no color results. By contrast, the isomeric dye-forming component containing an isopropyl group in the 3′-position produces a clearly visible, blue copy.

EXAMPLE 2

Hydrogen chloride is passed into a solution of 10 parts of isobutyl-(2-hydroxystyryl)-ketone and 16 parts of 4-dibenzylaminosalicylaldehyde in 120 parts of methanol at 40°–50° C. until saturation is reached. The mixture is then stirred for 3 hours at room temperature and cooled, the crystalline dye is isolated and the cyclization to give the dye-forming component is carried out as described in Example 1. 15 parts of 3-isopropyl-7-dibenzylamino-2,2'-spirodi-(2H-1-benzopyran) of the formula

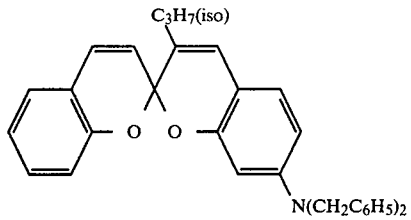

of melting point 119°–121° C., are obtained.

In contact with acidic substances, the compound develops a bluish grey coloration.

EXAMPLE 3

19 parts of n-propyl-(2-hydroxystyryl)-ketone and 19 parts of 4-N-pyrrolidinylsalicylaldehyde are reacted by a method similar to Example 1 to give the dye-forming component of the formula

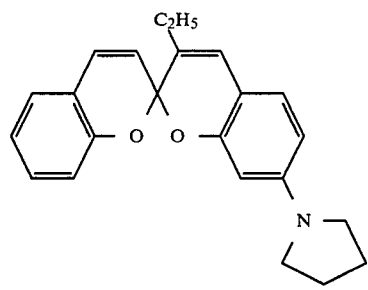

The yield of 3-ethyl-7-N-pyrrolidinyl-2,2'-spiro-di-(2H-1-benzopyran) is 9 parts and the compound has a melting point of 154°–156° C.

In contact with electron acceptors, the substance develops a bluish grey coloration.

EXAMPLE 4

9 parts of ethyl-(2-hydroxystyryl)-ketone and 9.5 parts of 4-H-pyrrolidinyl-salicylaldehyde are reacted as described in Example 1. After working up, 5 parts of 3-methyl-7-N-pyrrolidinyl-2,2'-spiro-di-(2H-1-benzopyran) of the formula

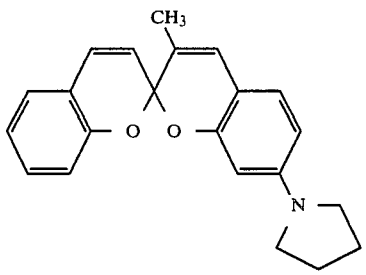

are obtained. The compound melts at 150°–152° C. and gives a bluish grey coloration in contact with acidic substances.

EXAMPLE 5

23 parts of 2-methyl-3-phenyl-7-dimethylaminobenzopyrylium tetrachloroferrate and 8 parts of 4-methoxysalicylaldehyde in 100 parts of alcohol are refluxed for 3½ hours. The mixture is then stirred for 12 hours at room temperature, after which the crystalline dye is isolated and the cyclization is carried out as described in Example 1. The yield of 3-phenyl-7-dimethylamino-7'-methoxy-2,2'-spiro-di-(2H-1-benzopyran) of the formula

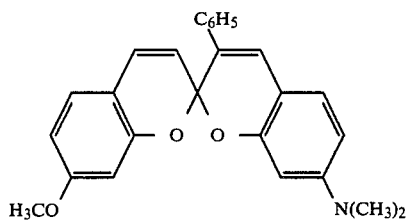

is 11 parts; the melting point is 148°–150° C.

In contact with acidic substances, the compound gives a green coloration.

EXAMPLES 6 TO 34

The dye-forming components of the formula

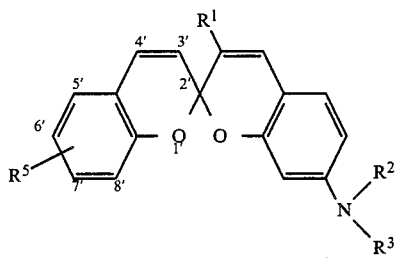

are obtained by methods similar to that of Example 1. The meanings of the substituents $R^1$, $R^2$, $R^3$ and $R^5$ are given in the Table which follows.

| Example | $R^1$ | $R^2$ | $R^3$ | $R^5$ | Hue |
|---|---|---|---|---|---|
| 6 | $CH_3$ | $CH_3$ | $CH_3$ | 6'-Cl | bluish grey |
| 7 | i-$C_3H_7$ | $CH_3$ | $CH_3$ | 6'-Br | bluish grey |
| 8 | $C_6H_5$ | $CH_3$ | $CH_3$ | 8'-$CO_2CH_3$ | bluish violet |
| 9 | $C_6H_5$ | $CH_3$ | $CH_3$ | 8'-$CO_2C_2H_5$ | bluish violet |
| 10 | $C_6H_5$ | $CH_3$ | $CH_3$ | 6'-$C_4H_9$(tert.) | blue |
| 11 | $C_6H_5$ | $CH_3$ | $CH_3$ | 6'-$NO_2$ | bluish violet |
| 12 | $C_6H_5$ | $CH_3$ | $CH_3$ | 6'-$CH_3$ | blue |
| 13 | $C_6H_5$ | —$(CH_2)_4$— | | 8'-$OCH_3$ | blue |

-continued

| Example | R¹ | R² | R³ | R⁵ | Hue |
|---|---|---|---|---|---|
| 14 | $C_6H_5$ | —(CH$_2$)$_4$— | | 7'-OCH$_3$ | bluish green |
| 15 | i-C$_4$H$_9$ | CH$_3$ | CH$_3$ | H | bluish grey |
| 16 | i-C$_5$H$_{11}$ | CH$_3$ | CH$_3$ | H | bluish grey |
| 17 | C$_{16}$H$_{33}$ | CH$_3$ | CH$_3$ | H | bluish grey |
| 18 | p-C$_6$H$_4$—CH$_3$ | CH$_3$ | CH$_3$ | H | blue |
| 19 | p-C$_6$H$_4$—Cl | CH$_3$ | CH$_3$ | H | blue |
| 20 | p-C$_6$H$_4$OCH$_3$ | CH$_3$ | CH$_3$ | H | blue |
| 21 | CH$_2$C$_6$H$_5$ | CH$_3$ | CH$_3$ | H | bluish grey |
| 22 | C$_2$H$_4$C$_6$H$_5$ | CH$_3$ | CH$_3$ | H | bluish grey |
| 23 | i-C$_3$H$_7$ | C$_3$H$_7$ | C$_3$H$_7$ | H | bluish grey |
| 24 | CH$_3$ | C$_{12}$H$_{25}$ | C$_{12}$H$_{25}$ | H | bluish grey |
| 25 | CH$_3$ | CH$_3$ | p-C$_6$H$_4$Cl | H | bluish grey |
| 26 | CH$_3$ | CH$_3$ | p-C$_6$H$_4$CH$_3$ | H | bluish grey |
| 27 | CH$_3$ | C$_2$H$_4$C$_6$H$_5$ | C$_2$H$_4$C$_6$H$_5$ | H | bluish grey |
| 28 | CH$_3$ | —(CH$_2$)$_5$— | | H | bluish grey |
| 29 | CH$_3$ | —(CH$_2$)$_2$O(CH$_2$)$_2$— | | H | bluish grey |
| 30 | CH$_3$ | —(CH$_2$)$_2$N(CH$_2$)$_2$—<br>\|<br>CH$_3$ | | H | bluish grey |
| 31 | CH$_3$ | (o-xylylene: H$_2$C—C$_6$H$_4$—CH$_2$) | | H | bluish grey |
| 32 | CH$_3$ | C$_2$H$_4$CN | CH$_2$C$_6$H$_5$ | H | bluish grey |
| 33 | CH$_3$ | C$_2$H$_4$CN | C$_2$H$_4$CN | H | bluish grey |
| 34 | CH$_3$ | C$_2$H$_4$Cl | C$_2$H$_4$Cl | H | bluish grey |
| 35 | CH$_3$ | C$_2$H$_4$OCH$_3$ | CH$_3$ | H | bluish grey |

EXAMPLE 36

The compound is prepared by methods similar to Example 1.

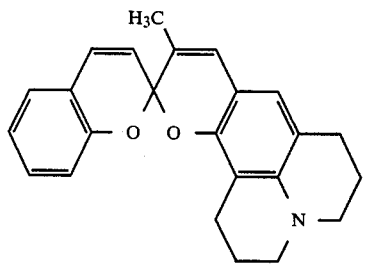

Hue: bluish grey

EXAMPLE 37

The compound is prepared by methods similar to Example 1.

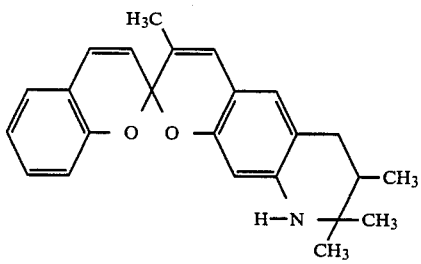

Hue: bluish grey

EXAMPLE 38

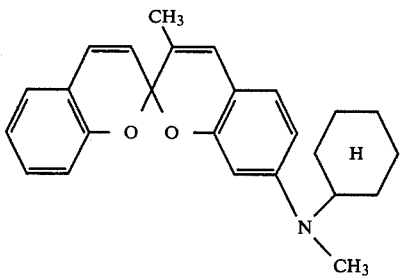

Hue: bluish grey

EXAMPLE 39

46 parts of 2-methyl-3-phenyl-7-dimethylaminobenzopyrylium tetrachloroferrate and 17 parts of 2-hydroxy-1-naphthaldehyde in 260 parts of methanol are refluxed for 2 hours. The crystalline dye is isolated, and is cyclized as described in Example 1 to give the dye-forming component. 18 parts of 3-phenyl-7-dimethylamino-spiro-(2H-1-benzopyran)-2,2'-2H-naphtho-(2,1-b)-pyran of the formula

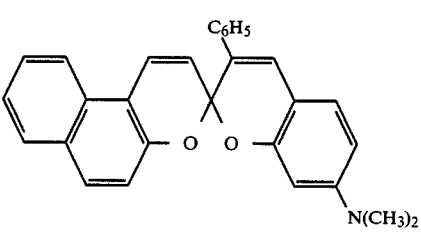

are obtained. The dye-forming component melts at 228°–230° and develops a bluish green coloration with electron acceptors.

EXAMPLES 40 TO 43

Dye-forming components of the formula

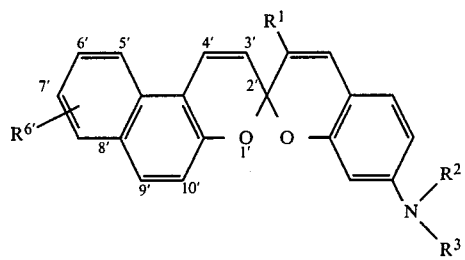

are obtained by a method similar to that of Example 39. The meanings of the substituents $R^1$, $R^2$, $R^3$ and $R^6$ are given in the Table which follows.

| Example | $R^1$ | $R^2$ | $R^3$ | $R^6$ | Hue |
|---|---|---|---|---|---|
| 40 | $C_6H_5$ | $CH_3$ | $CH_3$ | 7'-Cl | blue |
| 41 | $C_6H_5$ | —$(CH_2)_4$— | | 7'-Br | blue |
| 42 | $C_6H_5$ | $CH_3$ | $CH_3$ | 10'-$CO_2CH_3$ | blue |
| 43 | $C_6H_5$ | $CH_3$ | $CH_3$ | 10'-$CO_2C_2H_5$ | blue |

I claim:

1. A compound of the formula:

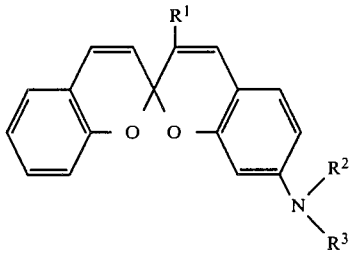

where $R^1$ is methyl or isopropyl and

is dibenzylamino.

2. The compound of claim 1 wherein $R^1$ is isopropyl and

is dibenzylamino.

3. A compound of the formula

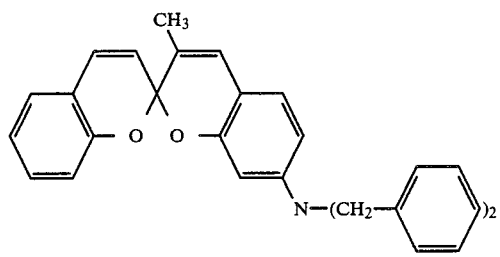

* * * * *